US00PP36151P2

(12) United States Plant Patent
Hansen

(10) Patent No.: US PP36,151 P2
(45) Date of Patent: Sep. 24, 2024

(54) ***HOSTA* PLANT NAMED 'Chance Encounter'**

(50) Latin Name: ***Hosta* hybrid (Tratt.)**
Varietal Denomination: Chance Encounter

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,633

(22) Filed: Nov. 29, 2023

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12
See application file for complete search history.

(56) References Cited

U.S. PATENT DOCUMENTS

PP22,413 P2 * 12/2011 Asch ..... A01H 6/12
Plt./353

OTHER PUBLICATIONS

Plants Galore Hosta 'Chance Encounter' retrieved on Apr. 8, 2024 at http://www.plantsgalore.com/hostas/cultivars/C/Hosta_Chance_Encounter.htm, 3 pp. (Year: 2024).*

* cited by examiner

*Primary Examiner* — June Hwu

(57) ABSTRACT

A new and distinct *Hosta* plant named 'Chance Encounter' of large, arching mounds of broadly ovate, bluish-green leaves having wide chartreuse margins upon emerging and maturing to yellowish-chartreuse margins. The variegation is also attractively displayed with numerous featherings of intermediate colors between the center and the leaf margins. The flowers are very pale purple to near white held just above the foliage beginning in late June for about three weeks. 'Chance Encounter' has an excellent, very large, mounded habit and is useful in the landscape, as a specimen or en masse.

3 Drawing Sheets

Botanical classification: *Hosta* hybrid (Tratt.).
Variety denomination: 'Chance Encounter'.

STATEMENT REGARDING PRIOR DISCLOSURES UNDER 37 CFR 1.77(b)(6)

*Hosta* 'Chance Encounter' was first introduced by the inventor as a non-enabling description through the International Cultivar Registration Authority registration in early 2023. No plants of 'Chance Encounter' have been sold or offered for sale in this country or anywhere in the world nor has any disclosure of the new plant been made more than one year prior to the filing date of this application.

BACKGROUND AND ORIGIN OF THE PLANT

The present invention relates to a new and distinct Hosta plant, *Hosta* 'Chance Encounter' hereinafter also referred to as the new plant or by the cultivar name, 'Chance Encounter'. *Hosta* 'Chance Encounter' was hybridized by the inventor on Jun. 25, 2015, at a wholesale perennial nursery in Zeeland, Michigan, USA. The female parent was a proprietary, unreleased sport of 'Elegans' known only as 14-SP-HOST-301 (not patented) and the male parent was 'Viking Ship'. The new plant was assigned the breeder code 15-274-1 and passed the initial evaluation in the summer of 2018. It has been asexually propagated by division at the same nursery since 2018, and also by careful shoot tip plant tissue culture with the resultant asexually propagated plants having retained all the same traits as the original plant.

*Hosta* 'Chance Encounter' is stable and reproduces true to type in successive generations of asexual reproduction.

There are more than 7,000 registered and established Hosta cultivars with The American Hosta Society which is the International Cultivar Registration Authority for the genus *Hosta*. Several of these have green leaf blades with variegated margins. The most similar Hosta cultivars known to the applicant are: 'Frances Williams' (not patented), 'Northern Exposure' (not patented), 'Earth Angel' (not patented), 'Seducer' U.S. Plant Pat. No. 22,413, and 'Wu-La-La' U.S. Plant Pat. No. 31,309.

'Frances Williams' maintains a more yellowish variegated margins throughout the growing season, and the leaves are susceptible to burning appearing as necrosis when mature. 'Northern Exposure' has more whitish variegated margin earlier in the season, and 'Chance Encounter' has a more yellowish variegated margin. 'Earth Angel' has a slightly larger habit and foliage with larger leaves that are less bullate and more cordate in shape, the leaf margins are more creamy-yellow in maturity. 'Seducer' has foliage that is more ovate, less glaucous, with a more acute apex, the leaf margins are repand, and the scape is taller extending well above the foliage with flowers that are more purplish. 'Wu-La-La' has a larger more cordate leaf that is less glaucous and the leaf margin is not as broad and of a more chartreuse hue.

The female parent has leaves that are streaked with bluish-green, cream, yellow, and chartreuse. The male parent has solid bluish-green leaves with a more acute apex and a slightly undulate margin.

Other *Hosta* cultivars may have individual traits similar to 'Chance Encounter' but the new plant differs from the above-listed cultivars and all other Hostas known to the applicant, by the combination of the following traits.

1. Leaves are large, broadly ovate, with broadly acute apices and cordate base.
2. Arching leaves mostly flat with a bluish-green center and chartreuse margin upon emerging and matures to a yellowish-chartreuse.
3. Between the leaf center and margins are numerous featherings of intermediate colors between the margin and center.
4. Flowers are pale purple to near white, densely arranged on scapes with the first flowers beginning to open just above the foliage in late June.
5. Large mounded habit is useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source, and direction may cause the appearance of minor variations in color.

The drawings show a six-year-old plant of 'Chance Encounter' in a trial garden at a nursery in Zeeland, MI with supplement fertilizer and water as needed.

DETAILED BOTANICAL DESCRIPTION

Figure 1:
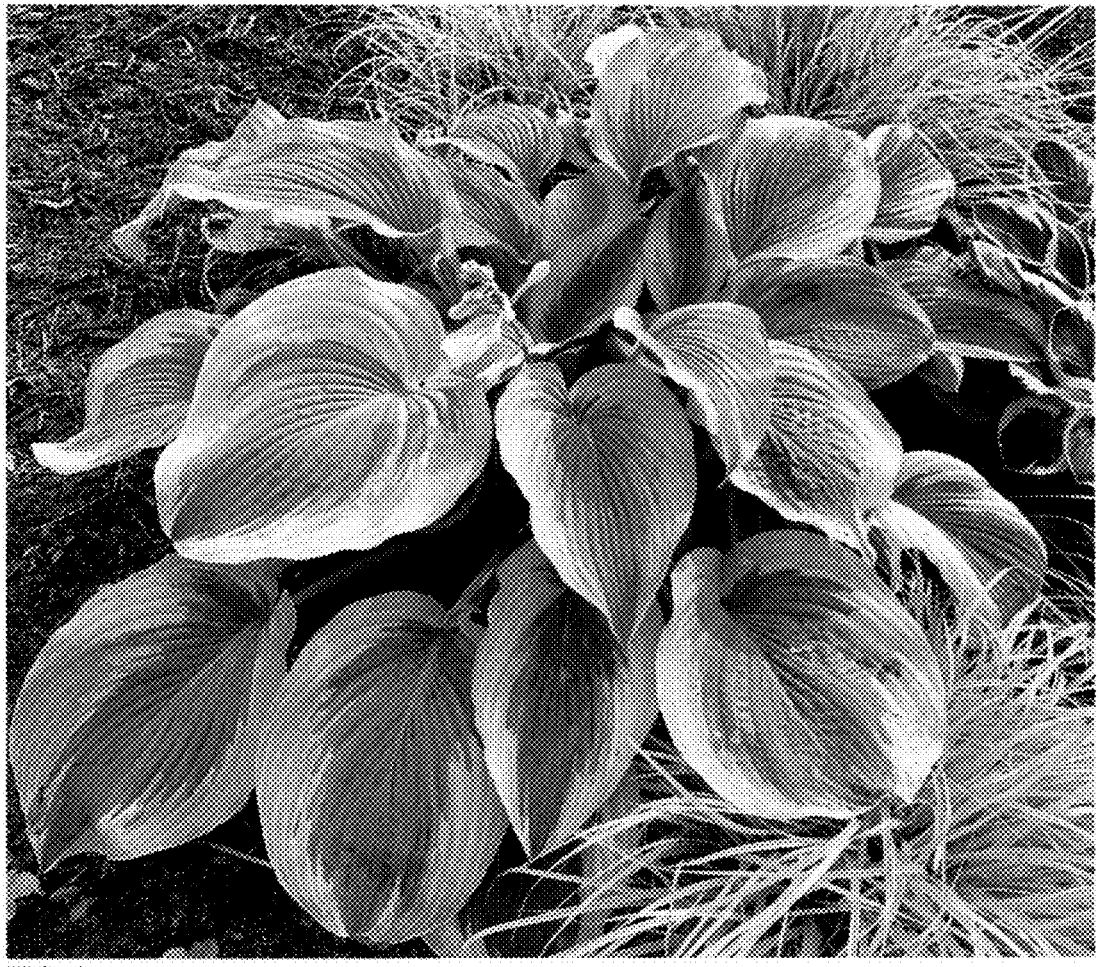
FIG. 1 shows the landscape foliage habit of a new plant at early flowering.
Figure 2:
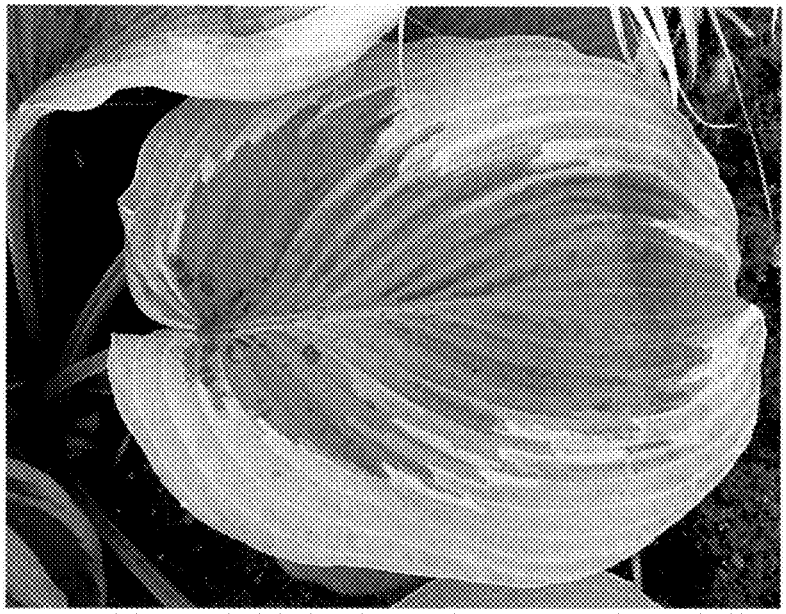
FIG. 2 shows a close-up of a leaf early in the season.
Figure 3:
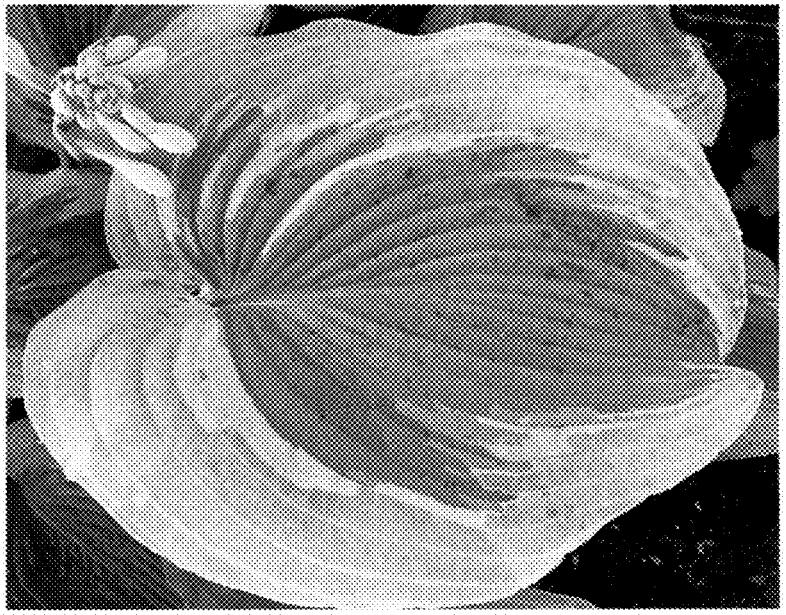
FIG. 3 shows a close-up of a leaf later in the season.
Figure 4:
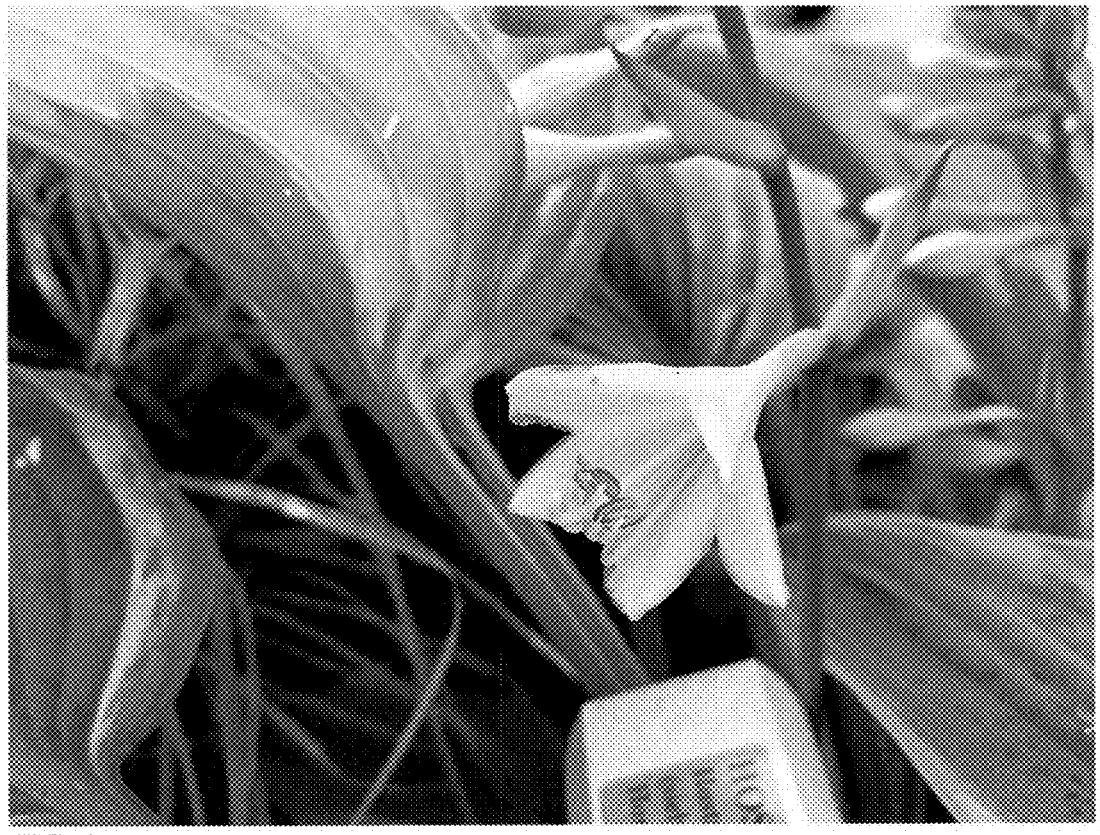
FIG. 4 shows a close-up of the flower scape with bracts, flowers, and buds.

The following descriptions and color references are based on the 2015 edition of The Royal Horticultural Society Colour Chart except where common dictionary terms are used. The new plant has not been observed under all possible environments. Those skilled in the art will appreciate that certain characteristics will vary with plants that are more mature or less mature. The phenotype may vary slightly with different environmental conditions, such as temperature, light, fertility, moisture, and maturity levels, but without any change in the genotype. The following observations and size descriptions are of a six-year-old plant in a shaded trial garden in Zeeland, Michigan with supplemental water and fertilizer.

*Botanical classification.*—*Hosta* x hybrid.

*Parentage.*—female or seed parent the proprietary streaked sport of 'Elegans' known as 14-SP-HOST-301; male or pollen parent 'Viking Ship'.

*Propagation.*—garden division and sterile shoot tip plant tissue culture.

*Time to initiate roots from tissue culture.*—about two to three weeks.

*Growth rate.*—moderate.

*Crop time.*—about three months to four months to finish during the spring in a one-liter container from rooted tissue culture plantlet.

*Rooting habit.*—fleshy, lightly branching.

*Root color.*—nearest RHS NN155C when actively growing.

*Plant shape and habit.*—hardy herbaceous perennial with a basal rosette of leaves emerging from rhizomes producing a medium-sized mound of arching petioles and leaves and erect scapes flowering just above the foliage.

*Plant size.*—foliage height to about 38 cm above the soil line to the top of the leaves, to about 56 cm tall to the top of the flowers, and to about 109 cm wide at the widest point slightly above the soil line.

*Foliage description.*—broadly ovate; broadly acute apex; cordate base; margin mostly flat, entire; glabrous and lightly glaucous on both surfaces; flexible but stiff; veins moderately impressed adaxial and costate abaxial.

*Leaf blade size.*—to about 28 cm long and about 20 cm wide about midway from the base; average about 25 cm long and 18 cm wide; margin width to about 5 cm wide, average 3.2 cm wide.

*Leaf blade color.*—early season and expanding adaxial margin nearest RHS 146D adaxial center nearest RHS 137A, adaxial intermediate colors comprising RHS 147B and RHS 138A; early season and expanding abaxial margin between RHS 147C and RHS 147D, abaxial center between RHS N138C and RHS 189B, abaxial intermediate colors between RHS 189B and RHS N138D; mid-season and mature adaxial margins variable nearest RHS 158D to nearest RHS 8C, adaxial center between RHS 137A and RHS 137B, adaxial intermediate colors comprising RHS 160D, RHS N138C, RHS 143C, between RHS 145C and RHS 160C, and between RHS 195C and RHS 194C; mid-season and mature abaxial margins variable nearest RHS 11D to nearest RHS 18C, adaxial center between RHS NN137C and RHS 189B, adaxial intermediate colors comprising RHS N138C, RHS 146D, RHS 193C, and between RHS 190C and RHS 191D.

*Petiole.*—glabrous and slightly glaucous both adaxial and abaxial; moderately concavo-convex; stiff; to 29 cm long and 16 mm wide at base and about 7 mm deep near base, average about 38 cm long and 20 mm wide.

*Petiole color.*—adaxial margins about 1 mm wide nearest RHS 158B, center between RHS 146B and RHS 146C; abaxial margins about 1 mm wide nearest RHS 158B, center nearest RHS 146D.

*Veins.*—twelve to fourteen pairs with midrib; parallel; moderately impressed adaxial; costate and smooth abaxial.

*Veins color.*—adaxial edge nearest RHS 155C, abaxial center nearest RHS 148C; abaxial secondary veins near the edge nearest RHS 158C and toward the center nearest RHS 160C.

*Flower description.*—Buds one to two days prior to opening: clavate with rounded apex and narrow tube base; about 42 mm long and 12 mm in diameter at the bulb with base narrowing in basal 18 mm to about 3 mm diameter.

*Bud color.*—between RHS NN155D and RHS 85D.

*Flowers.*—perfect; incomplete; flared campanulate; outwardly; to 61 mm long to exserted stigma; corolla about 51 mm long and 38 mm wide at tepal apices, fused in basal 28 mm, free in the distal 23 mm, corolla tube portion 20 mm long and 3 mm diameter, flower decreasing in size distally; persists for a normal period, usually about one day on the plant; mostly secund; flowers tightly arranged on the scape.

*Flowering period*.—scapes remain effective with flowers beginning in late June for about three weeks.

*Flower number*.—to about 33 flowers per scape.

*Fragrance*.—no detectable fragrance.

*Tepal*.—two identical sets of three; glabrous; entire margins; about 51 mm long and 13 mm wide slightly above fusion point; fused in basal 28 mm; clavate with broadly acute apex; entire margin; basal 20 mm forming tube.

*Tepal color*.—adaxial margin nearest RHS NN155D, center nearest RHS 84D with a 0.5 to 1.5 mm wide translucent edge; corolla tube base adaxial nearest RHS NN155C; abaxial nearest RHS NN155D with a very faint blush of nearest RHS 84D.

*Gynoecium*.—single; 61 mm long; superior. Style: cylindrical; about 55 mm long, 0.7 mm diameter; curved upward 90 degrees in distal 6 mm; color between RHS 145D and RHS 157D distally and nearest RHS 157D proximally. Stigma: puberulent; tri-lobed; about 1 mm across and 1 mm tall; color nearest RHS NN155A. Ovary: ellipsoidal; superior; apex rounded; base rounded to truncate; smooth; to about 5 mm long and 2.5 mm diameter in middle; color nearest RHS 145A.

*Androecium*.—six. Filaments: six, approximately 50 mm long and 0.5 mm in diameter; curved upward to about 90 degrees in the distal 7 mm; color between RHS 145D and RHS 157D distally and nearest RHS 157D proximally. Anthers: ellipsoidal, with rounded ends; basifixed, longitudinally dehiscent; about 4 mm long and 1.5 mm wide; color nearest RHS 195C. Pollen: spherical; less than 0.1mm long; abundant; color nearest RHS 17B.

*Pedicel*.—cylindrical; glabrous; glaucous; about 8 mm long and 2 mm diameter; aspect outwardly to slightly downwardly.

*Pedicel color*.—between RHS 146D and RHS 145D.

*Peduncle*.—cylindrical; usually one per mature division; about four per plant; glabrous; glaucous; erect; to about 56 cm tall, and about 7 mm in diameter at the base, average about 51 cm tall and 6 mm diameter at base.

*Peduncle color*.—proximal portion below leaves between RHS 146C and RHS 146D and distal portion nearest RHS N138C with a slight undertone of nearest RHS N187B.

*Inflorescence*.—flowering portion about 25 cm long and 12 cm wide; with small floral bracts subtending each flower.

*Floral bracts*.—each flower normally subtended by a single bract; lanceolate; acute apex and truncate base; entire margin; glabrous and glaucous abaxial and adaxial; to about 28 mm long 6 mm wide, decreasing distally.

*Bract color: at time of flowering adaxial nearest* 146D proximally and nearest RHS 137B distally; abaxial proximally nearest 148C, distally nearest RHS 137B with slight blush of nearest RHS 187A.

*Fruit*.—typically, tri-valved dehiscent capsule, rarely four-valved; cylindrical with apex apiculate to acute and truncate base; about 34 mm long and 7 mm diameter.

*Fruit color*.—nearest RHS N138B as maturing and between RHS 164C and RHS 161C when ripe.

*Seed*.—to 36 per capsule; endospermic; flattened-ellipsoidal wing surrounding embryo at one end of the ellipsoid; to about 11 mm long, 3 mm wide, and 1 mm thick at embryo.

*Seed color*.—nearest RHS 202A.

*Disease resistance*.—The thick glaucous leaves provide some resistance to slug feeding and the new plant appears to show resistance to leaf necrosis found in many large-leafed variegated Hosta. Other resistance or susceptibility to pests (including: *Odocoileus virginianus* and *Oryctotagus cuniculus*) and diseases common to Hostas is equal that typical of other cultivars.

*Plant growth*.—the new plant grows best and shows best coloration with plenty of moisture, adequate drainage and light shade, but is able to tolerate some drought when mature.

*Hardiness*.—at least from USDA zone 3 through 8, and other disease resistance is typical of that of other Hostas.

It is claimed:

1. A new and distinct *Hosta* plant named 'Chance Encounter' as herein described and illustrated.

* * * * *